(12) United States Patent
Duval et al.

(10) Patent No.: US 12,357,156 B2
(45) Date of Patent: Jul. 15, 2025

(54) DEVICES, SYSTEMS, AND METHODS FOR DETECTING FLUID FLOW

(71) Applicant: Boston Scientific Scimed, Inc., Maple Grove, MN (US)

(72) Inventors: George Wilfred Duval, Sudbury, MA (US); Scott Brechbiel, Acton, MA (US); Mike McGovern, Boston, MA (US); James Sawicki, Arlington, MA (US); Laura Christakis, Framingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 778 days.

(21) Appl. No.: 17/640,443

(22) PCT Filed: Sep. 30, 2020

(86) PCT No.: PCT/US2020/053357
§ 371 (c)(1),
(2) Date: Mar. 4, 2022

(87) PCT Pub. No.: WO2021/067325
PCT Pub. Date: Apr. 8, 2021

(65) Prior Publication Data
US 2022/0338812 A1    Oct. 27, 2022

Related U.S. Application Data

(60) Provisional application No. 62/908,844, filed on Oct. 1, 2019.

(51) Int. Cl.
*A61B 1/00* (2006.01)
*A61B 5/00* (2006.01)
(Continued)

(52) U.S. Cl.
CPC ...... *A61B 1/00135* (2013.01); *A61B 1/00097* (2022.02); *A61B 1/00148* (2022.02);
(Continued)

(58) Field of Classification Search
CPC ............ A61B 1/00135; A61B 1/00148; A61B 1/00097; A61B 1/00154; A61B 5/0261;
(Continued)

(56) References Cited

U.S. PATENT DOCUMENTS 5,305,121 A * 4/1994 Moll .................. A61B 1/05
348/45
5,368,015 A * 11/1994 Wilk .................. A61B 34/35
128/903

(Continued)

FOREIGN PATENT DOCUMENTS

| JP | 2008-520279 A | 6/2008 |
|---|---|---|
| JP | 2015-507948 A | 3/2015 |

(Continued)

OTHER PUBLICATIONS

International Search Report and Written Opinion issued in International Application No. PCT/US2020/053357, issued Jan. 11, 2021 (11 pages).

*Primary Examiner* — John P Leubecker
(74) *Attorney, Agent, or Firm* — Bookoff McAndrews PLLC (57) ABSTRACT

A medical device may comprise a plurality of prongs, each of the prongs having a sensor configured to detect a flow of fluid; and a sleeve disposed radially outward of the plurality of prongs. The sleeve may be configured to move proximally and distally relative to the plurality of prongs to transition the plurality of prongs from a contracted configuration to an expanded configuration.

20 Claims, 6 Drawing Sheets

(51) Int. Cl.
*A61B 5/026* (2006.01)
*A61B 8/00* (2006.01)
*A61B 8/06* (2006.01)

(52) U.S. Cl.
CPC ........ *A61B 1/00154* (2013.01); *A61B 5/0261* (2013.01); *A61B 5/6859* (2013.01); *A61B 8/06* (2013.01); *A61B 8/445* (2013.01)

(58) Field of Classification Search
CPC ......... A61B 5/6859; A61B 5/027; A61B 8/06; A61B 8/445
See application file for complete search history.

(56) References Cited

U.S. PATENT DOCUMENTS

| | | | | |
|---|---|---|---|---|
| 6,066,090 A * | 5/2000 | Yoon | .................. | A61B 17/3417 |
| | | | | 600/113 |
| 7,029,435 B2 * | 4/2006 | Nakao | ................ | A61B 1/00105 |
| | | | | 600/153 |
| 7,751,870 B2 * | 7/2010 | Whitman | ............. | A61B 90/361 |
| | | | | 600/407 |
| 10,835,211 B2 * | 11/2020 | Sette | .................... | A61B 5/6853 |
| 2012/0209086 A1 * | 8/2012 | Beute | .................... | A61B 5/7285 |
| | | | | 600/479 |
| 2015/0018848 A1 * | 1/2015 | Kappel | ............. | A61B 17/1285 |
| | | | | 606/140 |
| 2018/0360327 A1 * | 12/2018 | Duval | .................. | A61B 5/0205 |
| 2021/0338092 A1 * | 11/2021 | Akbari | ................ | A61B 5/4866 |

FOREIGN PATENT DOCUMENTS

| | | |
|---|---|---|
| JP | 2018-523534 A | 8/2018 |
| WO | 01/74263 A | 10/2001 |
| WO | WO 2013/112844 | 8/2013 |

\* cited by examiner

DEVICES, SYSTEMS, AND METHODS FOR DETECTING FLUID FLOW

CROSS-REFERENCE TO RELATED APPLICATIONS

This application is a National Stage under 35 U.S.C. § 371 of International Application No. PCT/US20/53357, filed Sep. 30, 2020, which claims the benefit of priority from U.S. Provisional Application No. 62/908,844, filed Oct. 1, 2019, which are incorporated by reference herein in their entireties.

TECHNICAL FIELD

The present disclosure relates generally to devices, systems, and methods for detecting fluid flow, and particularly to systems, apparatuses, and methods for detecting fluid flow during an endoscopic procedure.

BACKGROUND

Endoscopic procedures may be performed in order to treat a variety of conditions. For example, endoscopic procedures may be used to address issues relating to blood vessels. Such issues may arise independently or as a side effect of an endoscopic procedure. Blood vessels in the upper gastrointestinal (GI) tract that are either actively bleeding or are nonbleeding visible vessels may carry risks, including risks of bleeding or re-bleeding post procedure. Therefore, a need exists for systems, apparatuses, and methods for detecting flow in blood vessels in order to facilitate treatment of those blood vessels.

SUMMARY

In one example, a medical device may comprise a plurality of prongs, each of the prongs having a sensor configured to detect a flow of fluid; and a sleeve disposed radially outward of the plurality of prongs. The sleeve may be configured to move proximally and distally relative to the plurality of prongs to transition the plurality of prongs from a contracted configuration to an expanded configuration.

Any of the medical devise disclosed herein may have any of the following features. The sensor may disposed at a distal end of the prong. The distal ends of the plurality of prongs may be closer to one another in the contracted configuration than in the expanded configuration. Each of the plurality of prongs may be attached to a base. Each of the plurality of prongs may be attached to the base via a hinge. The base may be annular or tubular. The base may be configured to slidably receive an endoscope in an opening of the base. Distal ends of the prongs may be configured to be visible on a view using an imaging device of the endoscope. The sensor may include at least one of an ultrasound sensor or an optical sensor. In the contracted configuration, distal ends of the prongs may be closer to a central longitudinal axis of the sleeve than in the expanded configuration. Moving the sleeve proximally relative to the prongs may transition the plurality of prongs from the contracted configuration to the expanded configuration. Each of the prongs may include an indicator that communicates whether the respective sensor detects the flow of fluid. The indicator may include a light. In at least one of the contracted configuration or the expanded configuration, distal ends of the prongs may form a circular shape. The sleeve may be further configured to transition the plurality of prongs from the expanded configuration to a partially expanded configuration. The distal ends of the plurality of prongs may be closer to one another in the partially expanded configuration than in the expanded configuration. The distal end of each of the prongs may include a distal tip that is angled radially inward relative to a proximal portion of the prong.

In another example, a medical device may comprise: a detection device including a plurality of prongs, each of the prongs having a sensor at a distal end of the prong. The sensor may be configured to detect a flow of fluid. The detection device may be configured to transition from a first configuration to a second configuration. The distal ends of the plurality of prongs may be radially closer to one another in the first configuration than in the second configuration. The medical device may further comprise an endoscope. An outer surface of the endoscope may be received within an opening of the detection device.

Any of the medical devise disclosed herein may have any of the following features. The detection device may further include a sleeve disposed radially outward of the plurality of prongs. The sleeve may be configured to move proximally and distally relative to the plurality of prongs to transition the plurality of prongs from the first configuration to the second configuration.

An example method of treatment may comprise: positioning an endoscope having a detection at a treatment site in a body lumen of a patient; and transitioning a plurality of prongs of the detection device from a collapsed configuration to an expanded configuration. The distal ends of the plurality of prongs may be radially closer to one another in the collapsed configuration than in the expanded configuration. The method may also include using the detection device to determine whether there is a flow of fluid proximate to one or more of the plurality of prongs.

Any of the methods or devices disclosed herein may have any of the following features. The distal end of each of the plurality of prongs may include an ultrasound sensor or an optical sensor. Using the detection device may include using the ultrasound sensor or the optical sensor. The distal end of each of the plurality of prongs may include an indicator that communicates whether the ultrasound sensor or the optical sensor detects a flow of fluid.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." As used herein, the term "proximal" means a direction closer to an operator and the term "distal" means a direction further from an operator. The term "approximately" encompasses values within 10% of the provided value. Although endoscopes may be referred to herein, it will be appreciated that the aspects disclosed herein may be used in conjunction with a wide variety of devices, including but not limited to duodenoscopes, colonoscopes, bronchoscopes, laparoscopes, and/or ureteroscopes.

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

Endoscopic procedures may be utilized in order to treat blood vessels, such as those of the GI tract, including the upper GI tract. During such procedures, an operator may desire to detect blood flow and to administer a treatment. Although blood flow and blood vessels may be referenced herein, it will be appreciated that aspects of the disclosure below may also apply to other types of fluids, such as gastric fluids or other body fluids. However, if different tools must be passed down a single endoscope working channel in order to accomplish detection and treatment, it may be difficult to verify that a blood vessel has been appropriately treated. Furthermore, it may be desirable to verify that a treatment has been effective in ceasing or limiting a blood flow. The present disclosure includes detection devices that may fit over an external surface of a separate endoscope, or may be integrated into an endoscope, so that both the detection device and a treatment instrument may be visualized by an operator during detection and/or treatment. The detection device may remain in place during and after treatment, so that the detection device can confirm that a treatment was successful. The detection device may have several configurations, which may be employed during different phases of a procedure.

FIGS. 1A-1D show an exemplary detection device 10 in different configurations. Detection device 10 includes a sensor array 12. Sensor array 12 may include a plurality of prongs 14. For example, as shown in FIGS. 1A-1D, sensor array 12 may have six prongs 14. However, the number of prongs 14 shown in FIGS. 1A-1D is merely exemplary, and any suitable number of prongs 14 may be utilized. Prongs 14 may be arranged in an annular shape or in any other suitable shape (e.g., an oval, semi-circle, rectangular, square, or other shape). Furthermore, although sensor array 12 is shown with prongs 14, alternative structures may be used. For example, sensor array 12 may include an annular or semi-annular structure(s) instead of prongs 14. Each prong 14 may have one or more sensors 16. For example, each prong 14 is shown in FIGS. 1A-1D as having one sensor 16; however, other numbers of sensors 16 may be used, including multiple sensors on each prong 14. Further details of sensors 16 will be provided below.

In a contracted configuration, each of prongs 14 may extend generally along a longitudinal axis of detection device 10. Prongs 14 may be attached to a base 18 (see FIGS. 1C-1D). Base 18 may have a tubular or annular shape and may have a hollow center forming an opening. Prongs 14 may be arranged around base 18, e.g., equidistally arranged about base 18. For example, a proximal end of each of prongs 14 may be attached to base 18 (e.g., to a proximal portion of base 18 or another portion of base 18, such as a distal portion of base 18). Prongs 14 and base 18 may be separate pieces or may form a single, integral structure. Prongs 14 may be movable radially inward and outward relative to base 18. For example, prongs 14 may be attached to base 18 via a structure such as a hinge (e.g., a living hinge or another type of hinge) that may allow prongs 14 to move radially inward and/or outward. Each of prongs 14 may be biased to adopt a desired, set angle relative to base 18 and/or other portions of detection device 10, such as the longitudinal axis of device 10. For example, prongs 14 may be biased so that prongs 14 adopt an angle between 0 degrees and 90 degrees with respect to base 18 when prongs 14 are unconstrained. Prongs 14 may be biased by a connection with base 18 (e.g., a hinge) or by a material of prongs 14. For example, prongs 14 may be constructed from a shape memory material, such as nitinol, and may be configured to have a set angle relative a longitudinal axis of device 10. Each of prongs 14 may be biased to adopt a same angle as the others of prongs 14. Prongs 14 and/or base 18 (or another portion of detection device 10, such as sleeve 30, discussed below) may be configured such that prongs 14 are prevented from expanding radially outward past the neutral, unconstrained position. Prongs 14 may also be prevented from collapsing radially inward past a desired, set position (e.g., 0 degrees relative to base 18). For example, an outer surface of base 18 may limit radially inward movement of prong 14 and prevent prong 14 from moving radially inward of the surface of base 18. Sizes and shapes of prongs 14 may be varied depending upon an application of use. For example, a length of prongs 14 may be chosen to treat particular types of conditions or portions of the anatomy.

A prong 14 may have an angled distal tip 20 at a distal end of prong 14. For example, a distal tip 20 of prong 14 may protrude radially inward from the proximal, longitudinal arm portion 22 of prong 14 toward a central longitudinal axis of detection device 10 and/or base 18. An angle of distal tip 20 of prong 14 relative to longitudinal arm portion 22 of prong 14 may be approximately 90 degrees. A surface of distal tip 20 may face distally, along a direction of a central longitudinal axis of detection device 10. Sensor 16 may be disposed on the surface of distal tip 20 that faces generally distally. Sensor 16 may extend longitudinally through distal tip 20 so that sensor 16 additionally or alternatively is disposed on a surface of distal tip 20 that faces generally proximally. Distal tips 20 may form a circular shape or an approximately circular shape (see FIG. 1B). Prongs 14 may each have the same shape or may have different shapes from one another.

Detection device 10 may also include a sleeve 30. Sleeve 30 may be positioned radially outward of sensor array 12. For example, a central longitudinal axis of sleeve 30 may be coaxial with a central longitudinal axis of sensor array 12 (including base 18). Sleeve 30 may be movable relative to sensor array 12. For example, sleeve 30 may be longitudinally movable relative to sensor array 12. Additionally or alternatively, sleeve 30 may be rotationally movable relative to sensor array 12. For example, one or both of sleeve 30 and sensor array 12 may be movable via an actuation mechanism (not shown). Any suitable actuation mechanism that moves sleeve 30 proximally relative to array 12 may be used. As discussed in further detail below, sleeve 30 may be positioned so that it constrains prongs 14 so that prongs 14 extend approximately parallel to a longitudinal axis of detection device 10 (see FIG. 1A). When sleeve 30 is moved proximally so that prongs 14 extend distally of sleeve 30, prongs 14 may be free to adopt their neutral, unconstrained configuration, extending radially away from a central longitudinal axis of detection device 10 (see FIGS. 1C and 1D). Sleeve 30 may include features such as a smooth surface and/or an atraumatic distal edge for facilitating insertion of sleeve 30 into a subject.

Detection device 10 may be positioned on an exterior surface of a sheath 50 of a medical device 52. For example, sheath 50 may pass through sleeve 30, base 18, and/or prongs 14. Medical device 52 may be, for example, an endoscope, duodenoscope, bronchoscope, ureteroscope, colonoscope, laparoscope, catheter, tome, or other device. Sheath 50 may be permanently or removably attached to detection device 10. For example, sheath 50 and detection device 10 may form a single, integral unit. Alternatively, detection device 10 may be removable from sheath 50. Detection device 10 may be compatible for use with a variety of sheaths 50. For example, a size of detection device 10 may be varied, and different sizes of sheath 50 may be used in conjunction therewith.

Sheath 50 may be insertable into a body lumen of a patient and may have features such as an articulation joint (not shown) for steering a distal portion of sheath 50. Sheath 50 may have a distal tip 54, which may include optical features such as a camera 56 and/or a light source 58. Light source 58 may be, for example, an optical fiber, light emitting diode (LED), or other type of lighting device. Alternatively to camera 56, another kind of imaging device (e.g., optical fiber and/or lenses) may be used to transmit an image from a body lumen of a patient to an operator. Camera 56 may have image and/or video capture features. An output from camera 56 (or another visualization device) may be visible to an operator via an endoscopic view, using, e.g., a display monitor (not shown). Medical device 52 may include an operation portion (not shown) at a proximal portion of medical device 52.

Sheath 50 may also include a working channel 60, which may be a lumen that passes from a proximal end (not shown) to distal tip 54 of sheath 50. One or more tools may be passed through working channel 60 during an operation of medical device 52. Medical tools passed through working channel 60 may include clips, suturing devices, staplers, forceps, snares, ablation devices, needle knives, tomes, hemostatic agent delivery devices, etc. Sheath 50 may include any other desired feature and functionality useful in an endoscopic procedure, including suction, irrigation, etc.

Sheath 50 may be movable (e.g., slidable) relative to detection device 10. For example, sheath 50 may be moved longitudinally and/or rotationally relative to detection device 10. As discussed above, sensor array 12 and sleeve 30 of detection device 10 may be movable relative to one another. Each of sensor array 12, sleeve 30, and sheath 50 may be movable relative to one another. Locking mechanisms (not shown) may be used to selectively lock one or more of sensor array 12, sleeve 30, and sheath 50 with respect to one or more of the other components.

Figure 1A:
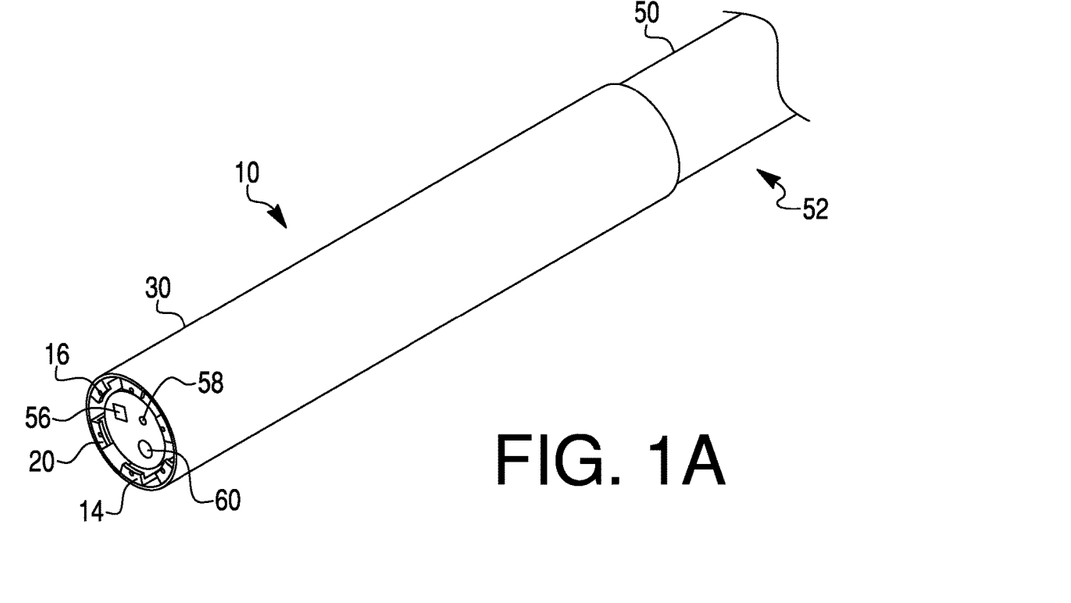
FIGS. 1A-1D depict an exemplary detection device.
Figure 3:
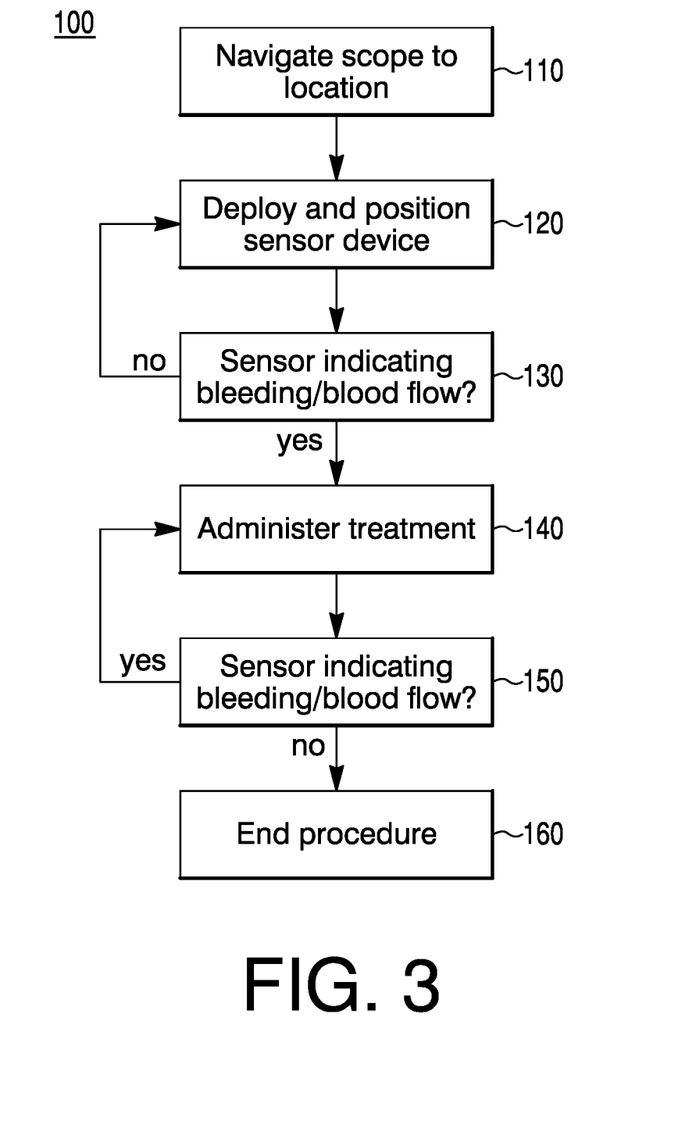
FIG. 3 is a flow chart depicting an exemplary process for detecting fluid flow.

During a procedure, sheath 50 and detection device 10 may be manipulated into different configurations during different phases of a procedure. FIG. 3 shows exemplary steps for a medical method 100. In step 110, sheath 50, with detection device 10 positioned thereabout, may be navigated through a body lumen to a site of a procedure. In step 110, detection device 10 and sheath 50 may be in a first configuration, shown in FIG. 1A. In the configuration of FIG. 1A, sleeve 30 may be positioned around prongs 14 so that prongs 14 are constrained by an inner surface of sleeve 30. For example, sleeve 30 may be positioned such that a distal end of sleeve 30 is longitudinally aligned with or approximately longitudinally aligned with a distal end of prongs 14. Prongs 14 may be constrained against base 18 so that prongs 14 are parallel to or approximately parallel to a central longitudinal axis of sleeve 30. Sheath 50 may be positioned so that distal tip 54 of sheath 50 is longitudinally aligned with or approximately longitudinally aligned with the distal ends of sleeve 30 and prongs 14. The configuration of FIG. 1A may facilitate insertion of sheath 50 and detection device 10 in a streamlined configuration and may also enable visualization of a procedural site via, for example, camera 56.

Figure 1B:
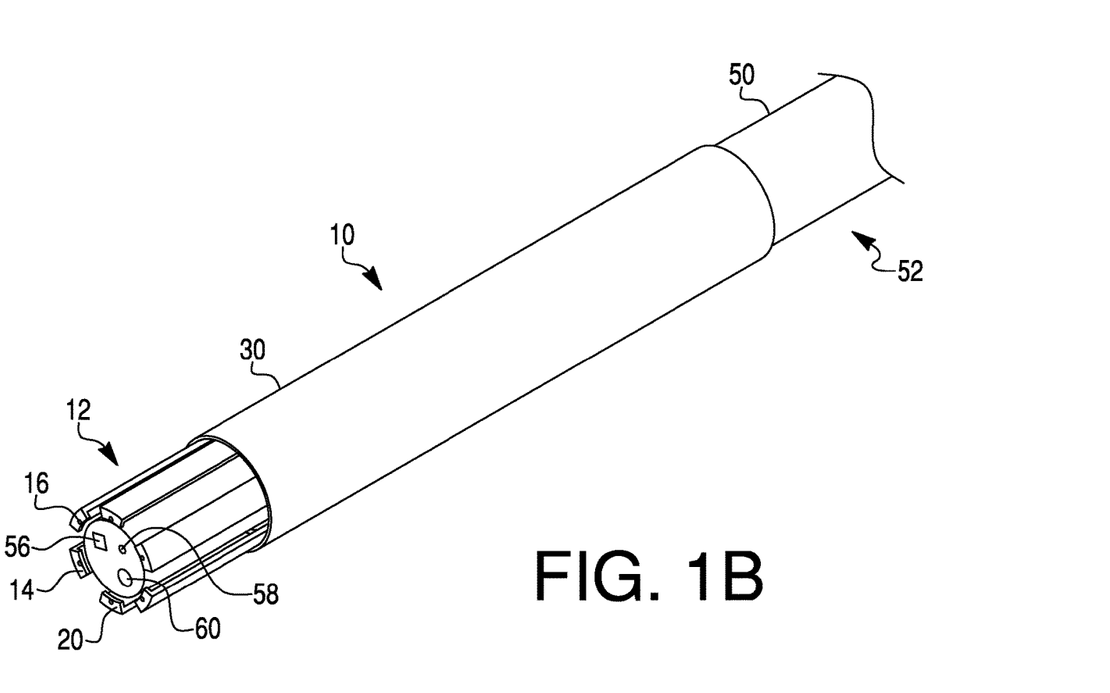
Figure 1C:
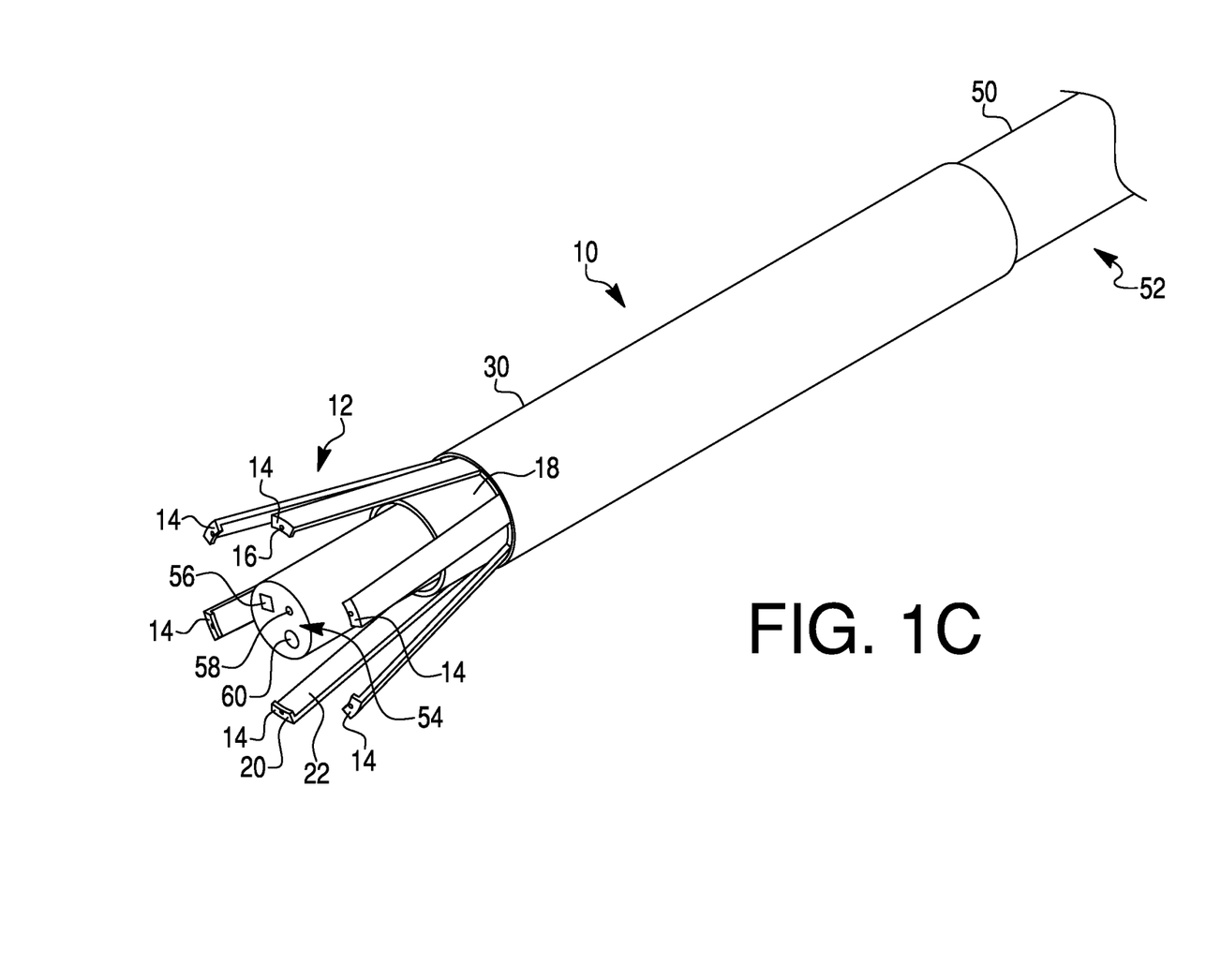
Figure 1D:
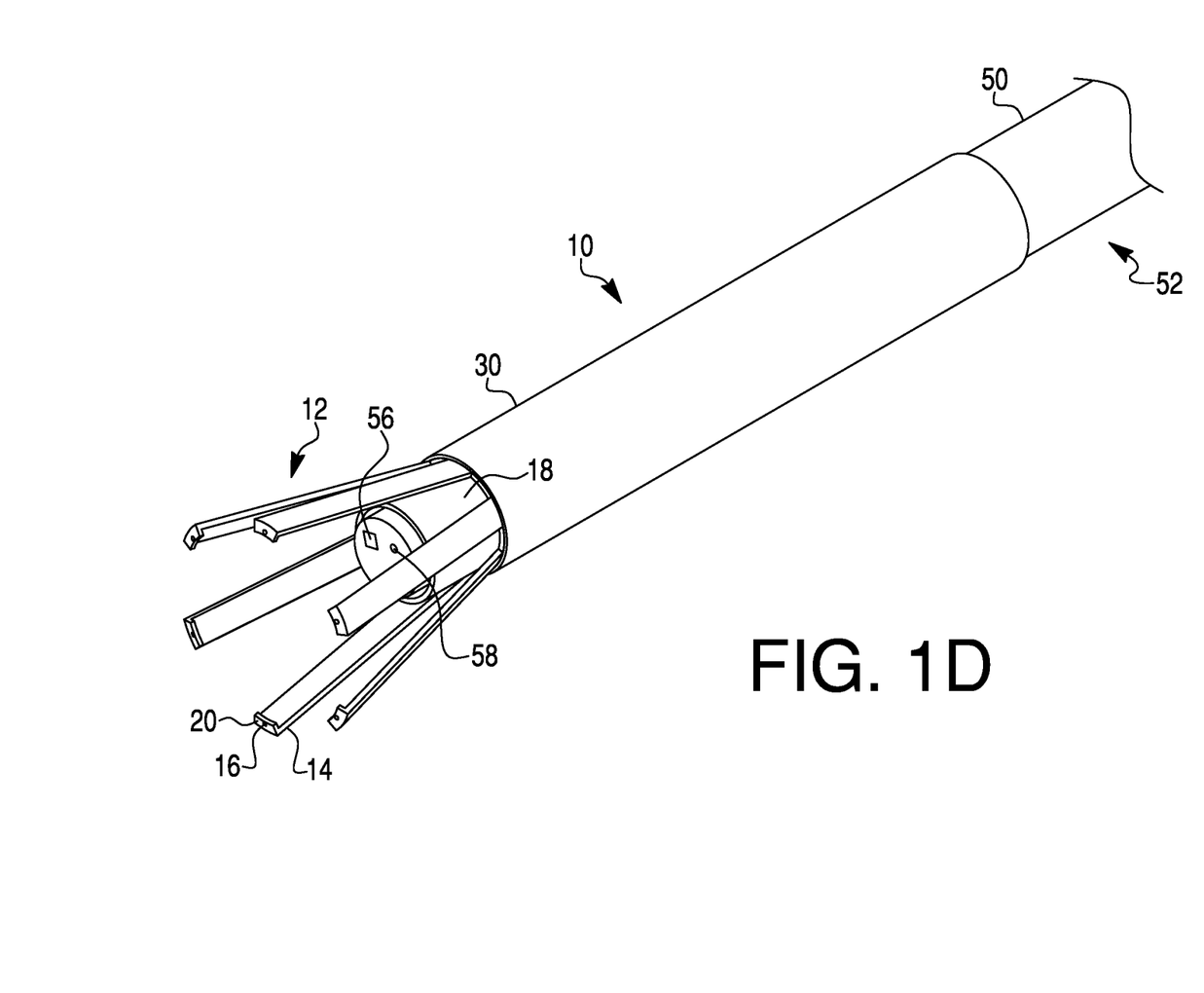

In step 120 of method 100, detection device 10 may be deployed and positioned, as shown in FIGS. 1B-1D. As shown in FIGS. 1B and 1C, sleeve 30 may be retracted via, for example, movement of sleeve 30 proximally relative to sensor array 12. As sleeve 30 is retracted proximally, prongs 14 may be permitted to expand radially outward relative to base 18 and/or sheath 50. Prongs 14 may, for example, expand radially after sleeve 30 is moved proximally of base 18 or of a distal portion of base 18. An amount of prongs 14 that extends radially outward may be adjustable by positioning sheath 50 in different longitudinal positions. For example, prongs 14 may be fully radially expanded when a distal end of sleeve 30 is longitudinally aligned with or proximal to a connection between prongs 14 and base 18 (e.g., longitudinally aligned with or proximal of a hinge connecting prongs 14 to base 18), and/or when a distal end of sleeve 30 is longitudinally aligned with or proximal to a proximalmost portion of prongs 14. When sleeve 30 is positioned more distally relative to prongs 14 (and/or base 18), prongs 14 may be somewhat constrained by sleeve 30 and may not fully expand. For example, prongs 14 may have a smaller angle relative to sleeve 30 and/or sheath 50 when prongs 14 are not fully expanded. An expanded radius of prongs 14 (i.e., the distance of distal tip 20 of prong 14 to a central longitudinal axis of array 12) may be adjusted to target areas of interest that are different sizes. Sleeve 30, prongs 14, and/or base 18 may have feedback features to provide information to an operator regarding a positioning of sleeve 30. For example, protrusions or indentations on sleeve 30, prongs 14, and/or base 18 may provide tactile feedback to an operator. Sleeve 30, prongs 14, and/or base 18 may also include stops or other features to prevent or limit sleeve 30 from being moved more proximally or distally than a maximum desired position.

As shown in FIG. 1D, sheath 50 may then be moved proximally relative to detection device 10 (i.e., relative to prongs 14, base 18, and sleeve 30). For example, sheath 50 may be moved proximally so that distal tip 54 is longitudinally aligned or approximately longitudinally aligned with a distal end of base 18. A retraction of sheath 50 in a proximal direction relative to detection device 10 may aid in visualizing a site of interest (e.g., using camera 56). Sheath 50 may be moved proximally using an actuation mechanism (not shown) or by simply pulling an entirety of shaft 50 proximally.

Figure 2A:
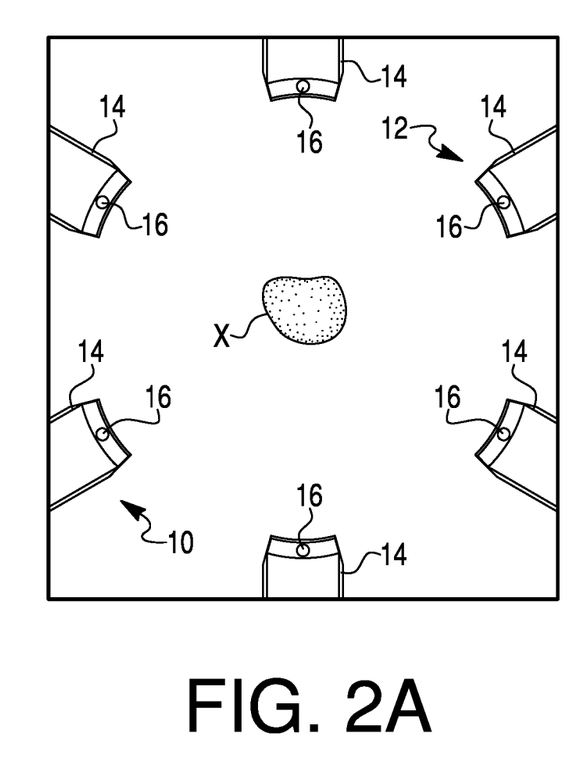
FIGS. 2A-2D depict exemplary operator views during utilization of the detection device of FIGS. 1A-1D.

In the configuration shown in FIG. 1D, an operator may be able to visualize distal tips 20 of prongs 14 (including sensors 16) via, for example, camera 56. As discussed above, sensors 16 may extend to a proximal-facing surface of distal tips 20. Alternatively, distal tips 20 may be transparent or translucent to allow for visualization of sensors 16. Sensors 16 may be configured in any manner suitable to permit visualization of sensors 16 or components or portions of sensors 16. For example, FIGS. 2A-2D may depict an operator's endoscopic view (e.g., via camera 56), while detection device 10 and sheath 50 are in the configuration of FIG. 1D. As shown in FIG. 2A, portions of prongs 14 including distal tips 20 may be visible on a perimeter of an endoscopic view, which may be shown on a display (not shown). Prongs 14 may be positioned around an area of interest. For example, FIGS. 2A-2D show prongs 14 positioned about a selected tissue, e.g., a suspected cecal post-polypectomy induced ulcer X. However, prongs 14 may be used in conjunction with a variety of conditions, such as a non-bleeding visible vessel, variceal bleeding, or active bleeding.

In step 130, detection device 10 may be utilized to determine whether bleeding or blood flow is present and/or detected. Sensors 16 may utilize any appropriate technology to determine whether bleeding is present. Sensors 16 may determine whether blood flow is present and may be configured to indicate a direction of blood flow or an amount of blood flow. Such information may be useful in determining what type of therapy to administer to a patient.

For example, sensors 16 may utilize ultrasound technology, such as Doppler ultrasound. Each of sensors 16 may include an ultrasound device. For example, sensor 16 may include a capacitive micromachined ultrasound transducer (CMUT) or a piezoelectric micromachined ultrasound transducer (PMUT). For example, an ultrasound device may emit ultrasonic waves, which are scattered by moving red blood cells that the waves contact. The waves may return to the receiver having a frequency that has been altered by the Doppler Effect. A plug flow algorithm or any other suitable algorithm may be utilized in order to determine whether blood flow is present.

Additionally or alternatively, sensors 16 may utilize an optical perfusion sensor, such as those described in U.S. Patent Application No. 62/522,168, incorporated by reference herein in its entirety. For example, wavelengths of approximately 530 nanometer or approximately 420 nanometers may be used because those wavelengths are where light absorption for deoxy and oxyhemoglobin peaks. A 530 nanometer green light may penetrate deep into tissue and to the muscularis layer of an intestine. A 530 nanometer green light may also have a high signal-to-noise ratio and relative freedom from artifacts, as compared to other wavelengths. Sensors 16 may include an illuminating device (e.g., an LED that emits 530 nanometer green light) and a receiver device (e.g., a photodiode). Sensor 16 may provide a pulsatile representation of a plethysmograph, which may show a time graph of blood flow. For example, sensor 16 may measure how light waves emitted by the illuminating device are absorbed and reflected by hemoglobin in an area of interest.

A perfusion index may be determined based on data from sensor 16. A perfusion index may include a ratio of an amount of pulsatile light (which may be an AC component) measured by sensor 16 to an amount of total light (which may be a DC component) measured by sensor 16. For example, a perfusion index may be calculated according to the following equation:

$$\text{Perfusion Index (\%)} = P = \frac{\text{Pulsatile } (AC \text{ Component})}{\text{Total Light } (DC \text{ Component})} \times 100\%$$

A perfusion index of less than 2% may be indicative of hypoperfusion. A perfusion index of between 2% and 4% may be indicative of moderate perfusion. A perfusion index between 4% and 8% may be indicative of sufficient perfusion. A perfusion index over 8% may be indicative of hyper-perfusion. The above equation is merely exemplary. Any other suitable method may be used to calculate an amount of perfusion in a tissue of a GI tract. The ranges above are also merely exemplary. The ranges may differ based on patient, location, measurement tool, equation used, or other factors. Although a perfusion index is provided, alternative measurements or algorithms may be utilized in order to determine whether blood flow exists.

Each of sensors 16 (which may be on distal tips 20) may include an indicator 200. Indicator 200 may be, for example, a light, such as an LED light, disposed on distal tip 20 and facing proximally so as to be visible via camera 56. Indicator 200 may be activated where a sensor 16 detects blood flow. For example, indicator 200 may light up or turn a different color (e.g., green, where an indicator not detecting blood flow is yellow, white, another color, or turned off). For example, if sensor 16 includes an ultrasound sensor (e.g., a CMUT or PMUT), an algorithm such as a plug flow algorithm may be used. If blood flow is detected, indicator 200 may be activated. If sensor 16 includes a perfusion sensor, indicator 200 may be activated if moderate perfusion, sufficient perfusion, or hyper-perfusion is detected (using, e.g., the parameters above). For example, indicator 200 may be activated if sensor 16 indicates a perfusion index greater than or equal to 2%. Indicator 200 may be binary and only indicate whether or not blood flow is detected. Additionally or alternatively, indicator 200 may indicate gradations in perfusion using, e.g., color variations in an LED light of sensor 60.

Figure 2B:
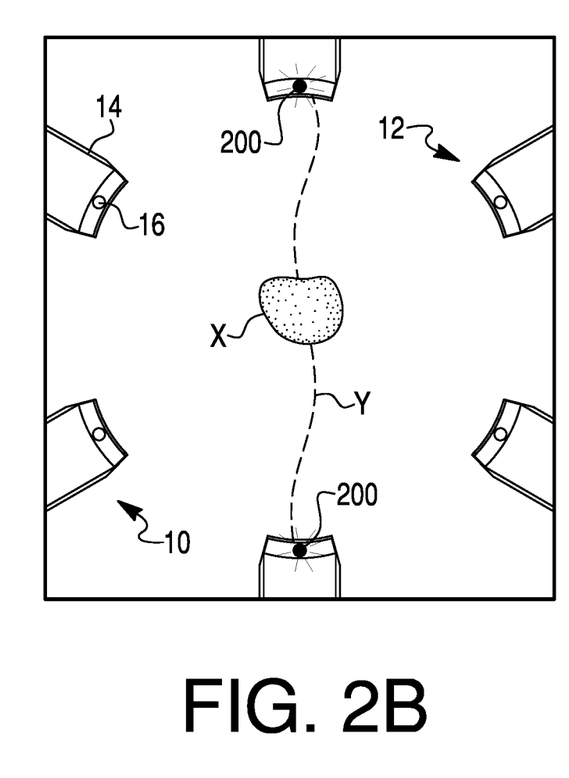

As shown in FIG. 2B, indicators 200 activate to communicate (e.g., indicate or suggest) a path of a blood flow and therefore a blood vessel. For example, in FIG. 2B the indicators 200 at the top and bottom of the endoscopic view are activated (e.g., lit up), suggesting the presence of a non-bleeding blood vessel (or another feature) traveling in a vertical direction of the endoscopic view shown in FIG. 2B. Such a blood vesselY is shown in dotted lines on FIG. 2B. Alternatively, mechanisms other than a light may be used. For example, a display viewable by an operator may include a diagram of portions of detection device 10 (e.g., of distal tips 20 or other portions of prongs 14), and the diagram may indicate which of sensors 16 show blood flow. In such an example, the distal tips 20 themselves may not include a physical indicator 200, and blood flow may instead be indicated virtually on a display. In a case where virtual indicators are used, a display device may also map a suspected blood vessel (e.g., using dotted lines as shown in FIG. 2B for vesselY). Additionally, or alternatively, light may be projected from portions of detection device 10 onto tissue of a patient to show a blood vessel location. Additionally, or alternatively, an operator of detection device 10 may infer a position of a blood vessel based on indicators 200 without detection device 10 explicitly showing a path of a suspected blood vessel. Although FIG. 2B shows two indicators 200 activated, one indicator 200 or more than two indicators 200 may be activated. In such cases, detection device 10 may be repositioned to obtain more information and/or a path of blood flow may be inferred from the activated indicator(s) 200.

Figure 2C:
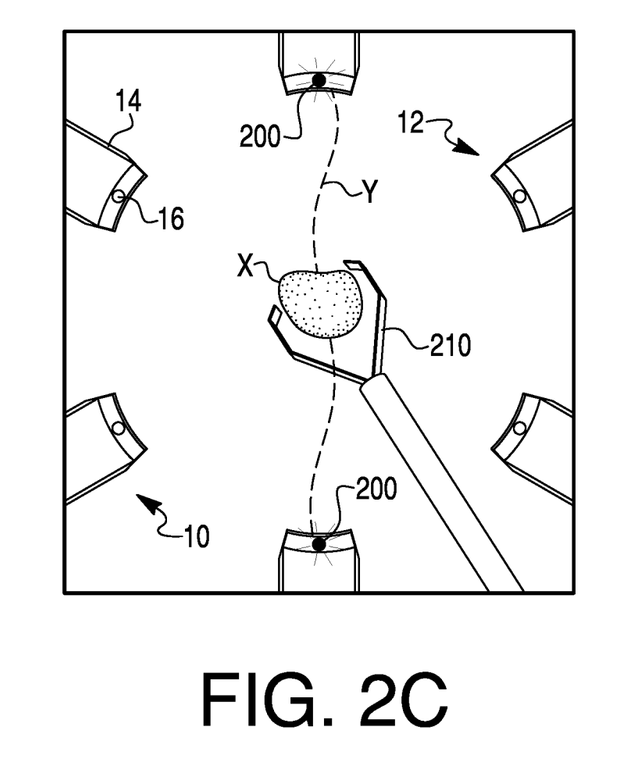

If blood flow is detected in step 130, then treatment may be administered in step 140. For example, as shown in FIG. 2C, a tool 210 may be advanced through working channel 60 and out of a distal opening of working channel 60. As shown in FIG. 2C, tool 210 may be a clip. Alternatively, tool 210 may be one or more of the following: suturing devices, staplers, forceps, snares, ablation devices, needle knives, tomes, hemostatic agent delivery devices, etc. More than one tool 210 may be advanced through working channel 60 simultaneously. Tool 210 may be navigated toward a suspected blood vessel suggested by indicators 200. For example, a clip may be positioned over the blood vessel, as shown in FIG. 2C. During treatment in step 130, detection device 10 may remain in place so that an operator can continue to visualize the bleeding or blood flow indicated by sensors 16 and/or indicators 200. For example, indicators 200 may continue to be activated during treatment. Because detection device 10 is positioned over sheath 50, tool 210 may be manipulated without displacing detection device 10 or without reducing availability of working channel 60.

During step 130, sheath 50 may be moved proximally and/or distally relative to detection device 10. For example, sheath 50 may be actuated between the configurations shown in FIGS. 1C and 1D or to other configurations wherein sheath 50 is positioned differently with respect to detection device 10. Such movement of sheath 50 may enable an operator to obtain different views (e.g., via camera 56) or to use tool 210 as desired.

Figure 2D:
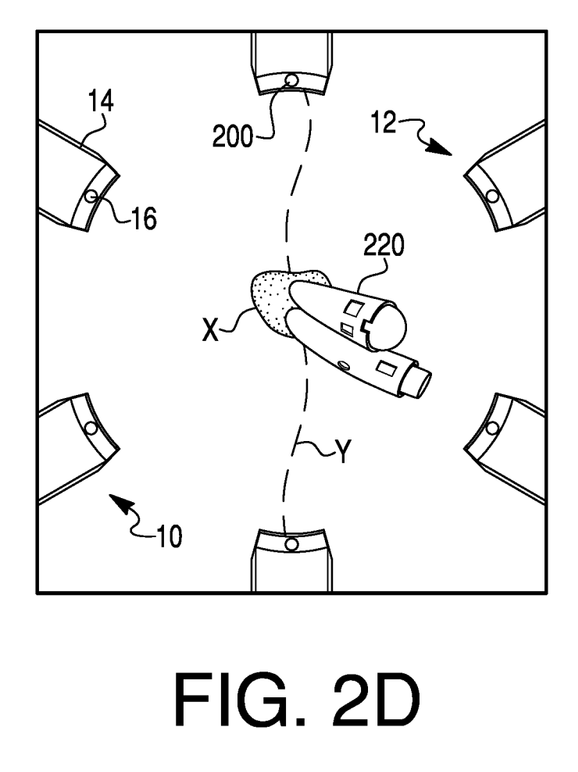

After treatment has been administered in step 140, detection device 10 may be utilized in step 150 to determine whether bleeding or blood flow has been effectively treated and/or eliminated. As shown in FIG. 2D, a device, such as clip 220, may have been positioned on a treated area in step 130. Sensors 16 and/or indicators 200 may have continued to be operational during steps 130 and 140. If sensors 16 and/or indicators 200 were deactivated during the course of performing steps 130 and/or 140, sensors 16 and/or indicators 200 may be reactivated during step 150. If indicators 200 do not indicate blood flow (e.g., do not light up or change color or otherwise indicate blood flow detected by sensors 16), then a procedure may be ended in step 160 because the procedure effectively limited or eliminated bleeding or blood flow. If indicators 200 indicate blood flow, then further treatment may be administered in step 140.

The steps of the method 100 above are not exclusive, and additional steps may be utilized or certain steps may be omitted. Steps of method 100 may be performed in alternative orders and may be repeated. The specific configurations shown in FIGS. 1A-1D are merely exemplary, and components of detection device 10 and sheath 50 may be alternatively positioned in order to achieve goals of a procedure.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A medical device, comprising
   a plurality of prongs, each of the prongs having a sensor configured to detect a flow of fluid, and wherein each of the prongs includes an indicator that communicates whether the respective sensor detects the flow of fluid; and
   a sleeve disposed radially outward of the plurality of prongs;
   wherein the sleeve is configured to move proximally and distally relative to the plurality of prongs to transition the plurality of prongs from a contracted configuration to an expanded configuration.

2. The medical device of claim 1, wherein the sensor is disposed at a distal end of the prong, and wherein the distal ends of the plurality of prongs are closer to one another in the contracted configuration than in the expanded configuration.

3. The medical device of claim 1, wherein each of the plurality of prongs is attached to a base.

4. The medical device of claim 3, wherein each of the plurality of prongs is attached to the base via a hinge.

5. The medical device of claim 3, wherein the base is annular or tubular.

6. The medical device of claim 3, wherein the base is configured to slidably receive an endoscope in an opening of the base.

7. The medical device of claim 6, wherein distal ends of the prongs are configured to be visible on a view using an imaging device of the endoscope.

8. The medical device of claim 1, wherein the sensor includes at least one of an ultrasound sensor or an optical sensor.

9. The medical device of claim 1, wherein, in the contracted configuration, distal ends of the prongs are closer to a central longitudinal axis of the sleeve than in the expanded configuration.

10. The medical device of claim 1, wherein moving the sleeve proximally relative to the prongs transitions the plurality of prongs from the contracted configuration to the expanded configuration.

11. The medical device of claim 1, wherein the indicator includes a light.

12. The medical device of claim 1, wherein, in at least one of the contracted configuration or the expanded configuration, distal ends of the prongs form a circular shape.

13. The medical device of claim 12, wherein the sleeve is further configured to transition the plurality of prongs from the expanded configuration to a partially expanded configuration, wherein the distal ends of the plurality of prongs are closer to one another in the partially expanded configuration than in the expanded configuration.

14. The medical device of claim 12, wherein the distal end of each of the prongs includes a distal tip that is angled radially inward relative to a proximal portion of the prong.

15. A medical device, comprising
   a detection device including a plurality of prongs, each of the prongs having a sensor at a distal end of the prong, wherein the sensor is configured to detect a flow of fluid, wherein the distal end of each of the plurality of prongs includes an indicator that communicates whether the respective sensor detects the flow of fluid, wherein the detection device is configured to transition from a first configuration to a second configuration, and wherein the distal ends of the plurality of prongs are radially closer to one another in the first configuration than in the second configuration; and
   an endoscope, wherein an outer surface of the endoscope is received within an opening of the detection device.

16. The medical device of claim 15, wherein the detection device further includes a sleeve disposed radially outward of the plurality of prongs, and wherein the sleeve is configured to move proximally and distally relative to the plurality of prongs to transition the plurality of prongs from the first configuration to the second configuration.

17. The medical device of claim 15, wherein the sensor includes at least one of an ultrasound sensor or an optical sensor.

18. The medical device of claim 15, wherein each of the plurality of prongs is attached to a base, and wherein the base has an opening configured to slidably receive the endoscope therein.

19. The medical device of claim 18, wherein the endoscope includes an imaging device, and wherein distal ends of the prongs of the detection device are configured to be visible on a view using the imaging device.

20. A method of treatment comprising:
   positioning an endoscope having a detection device at a treatment site in a body lumen of a patient, wherein the detection device includes a plurality of prongs, wherein a distal end of each of the plurality of prongs includes an ultrasound sensor or an optical sensor;

transitioning the plurality of prongs of the detection device from a collapsed configuration to an expanded configuration, wherein the distal ends of the plurality of prongs are radially closer to one another in the collapsed configuration than in the expanded configuration; and using the ultrasound sensor or the optical sensor of the detection device to determine whether there is a flow of fluid proximate to one or more of the plurality of prongs, and wherein the distal end of each of the plurality of prongs includes an indicator that communicates whether the respective sensor detects the flow of fluid.

* * * * *